United States Patent [19]

Johnston et al.

[11] Patent Number: 5,639,650

[45] Date of Patent: Jun. 17, 1997

[54] CDNA CLONE FOR SOUTH AFRICAN ARBOVIRUS NO. 86

[75] Inventors: Robert E. Johnston; Nancy L. Davis, both of Chapel Hill; Dennis A. Simpson, Carrboro, all of N.C.

[73] Assignee: The University of North Carolina at Chapel Hill, Chapel Hill, N.C.

[21] Appl. No.: 446,932

[22] Filed: May 23, 1995

[51] Int. Cl.$^6$ .............................. C12N 7/04; C12N 15/86
[52] U.S. Cl. ..................... 435/236; 435/320.1; 536/23.1; 536/23.72
[58] Field of Search ................ 435/320.1, 235.1, 435/172.1, 172.3, 236; 536/23.1, 23.72

[56] References Cited

U.S. PATENT DOCUMENTS

| | | | |
|---|---|---|---|
| 4,650,764 | 3/1987 | Temin et al. | 435/240.2 |
| 5,185,440 | 2/1993 | Davis et al. | 536/23.72 |
| 5,217,879 | 6/1993 | Huang et al. | 435/69.1 |

FOREIGN PATENT DOCUMENTS

WO92/10578  6/1992  WIPO.

OTHER PUBLICATIONS

Strauss et al., "The Alphaviruses: Gene Expression, Replication, and Evolution", Microbiol. Rev., vol. 58, No. 3, pp. 491–562.

Russell, et al., *Sindbis Virus Mutations Which Coordinately Affect Glycoprotein Processing, Penetration, And Virulence In Mice*, Journal of Virology, vol. 63, No. 4, Apr. 1989, pp. 1619–1629.

*Primary Examiner*—David Guzo

[57] ABSTRACT

The present invention provides a recombinant DNA comprising a cDNA coding for an infectious South African Arbovirus No. 86 (S.A.AR86) virus RNA transcript and a heterologous promoter positioned upstream from the cDNA and operatively associated therewith. The present invention also provides an infectious RNA transcript encoded by the cDNA, and infectious attenuated viral particles containing the RNA transcript encoded by the cDNA.

25 Claims, 1 Drawing Sheet

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 11663 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( x i ) SEQUENCE DESCRIPTION: SEQ ID NO:1:

```
ATTGGCGGCG  TAGTACACAC  TATTGAATCA  AACAGCCGAC  CAATTGCACT  ACCATCACAA      60

TGGAGAAGCC  AGTAGTTAAC  GTAGACGTAG  ACCCTCAGAG  TCCGTTTGTC  GTGCAACTGC     120

AAAAGAGCTT  CCCGCAATTT  GAGGTAGTAG  CACAGCAGGT  CACTCCAAAT  GACCATGCTA     180

ATGCCAGAGC  ATTTTCGCAT  CTGGCCAGTA  AACTAATCGA  GCTGGAGGTT  CCTACCACAG     240

CGACGATTTT  GGACATAGGC  AGCGCACCGG  CTCGTAGAAT  GTTTTCCGAG  CACCAGTACC     300

ATTGCGTTTG  CCCCATGCGT  AGTCCAGAAG  ACCCGGACCG  CATGATGAAA  TATGCCAGCA     360

AACTGGCGGA  AAAAGCATGT  AAGATTACAA  ACAAGAACTT  GCATGAGAAG  ATCAAGGACC     420

TCCGGACCGT  ACTTGATACA  CCGGATGCTG  AAACGCCATC  ACTCTGCTTC  CACAACGATG     480

TTACCTGCAA  CACGCGTGCC  GAGTACTCCG  TCATGCAGGA  CGTGTACATC  AACGCTCCCG     540

GAACTATTTA  CCACCAGGCT  ATGAAAGGCG  TGCGGACCCT  GTACTGGATT  GGCTTCGACA     600

CCACCCAGTT  CATGTTCTCG  GCTATGGCAG  GTTCGTACCC  TGCATACAAC  ACCAACTGGG     660
```

-continued

```
CCGACGAAAA AGTCCTTGAA GCGCGTAACA TCGGACTCTG CAGCACAAAG CTGAGTGAAG    720
GCAGGACAGG AAAGTTGTCG ATAATGAGGA AGAAGGAGTT GAAGCCCGGG TCACGGGTTT    780
ATTTCTCCGT TGGATCGACA CTTTACCCAG AACACAGAGC CAGCTTGCAG AGCTGGCATC    840
TTCCATCGGT GTTCCACTTG AAAGGAAAGC AGTCGTACAC TTGCCGCTGT GATACAGTGG    900
TGAGCTGCGA AGGCTACGTA GTGAAGAAAA TCACCATCAG TCCCGGGATC ACGGGAGAAA    960
CCGTGGGATA CGCGGTTACA AACAATAGCG AGGGCTTCTT GCTATGCAAA GTTACCGATA   1020
CAGTAAAAGG AGAACGGGTA TCGTTCCCCG TGTGCACGTA TATCCCGGCC ACCATATGCG   1080
ATCAGATGAC CGGCATAATG GCCACGGATA TCTCACCTGA CGATGCACAA AAACTTCTGG   1140
TTGGGCTCAA CCAGCGAATC GTCATTAACG GTAAGACTAA CAGGAACACC AATACCATGC   1200
AAAATTACCT TCTGCCAATC ATTGCACAAG GGTTCAGCAA ATGGGCCAAG GAGCGCAAAG   1260
AAGATCTTGA CAATGAAAAA ATGCTGGGCA CCAGAGAGCG CAAGCTTACA TATGGCTGCT   1320
TGTGGGCGTT TCGCACTAAG AAAGTGCACT CGTTCTATCG CCCACCTGGA ACGCAGACCA   1380
TCGTAAAAGT CCCAGCCTCT TTTAGCGCTT TCCCCATGTC ATCCGTATGG ACTACCTCTT   1440
TGCCCATGTC GCTGAGGCAG AAGATGAAAT TGGCATTACA ACCAAAGAAG GAGGAAAAAC   1500
TGCTGCAAGT CCCGGAGGAA TTAGTTATGG AGGCCAAGGC TGCTTTCGAG GATGCTCAGG   1560
AGGAATCCAG AGCGGAGAAG CTCCGAGAAG CACTCCCACC ATTAGTGGCA GACAAAGGTA   1620
TCGAGGCAGC TGCGGAAGTT GTCTGCGAAG TGGAGGGGCT CCAGGCGGAC ACCGGAGCAG   1680
CACTCGTCGA AACCCCGCGC GGTCATGTAA GGATAATACC TCAAGCAAAT GACCGTATGA   1740
TCGGACAGTA TATCGTTGTC TCGCCGATCT CTGTGCTGAA GAACGCTAAA CTCGCACCAG   1800
CACACCCGCT AGCAGACCAG GTTAAGATCA TAACGCACTC CGGAAGATCA GGAAGGTATG   1860
CAGTCGAACC ATACGACGCT AAAGTACTGA TGCCAGCAGG AAGTGCCGTA CCATGGCCAG   1920
AATTCTTAGC ACTGAGTGAG AGCGCCACGC TTGTGTACAA CGAAAGAGAG TTTGTGAACC   1980
GCAAGCTGTA CCATATTGCC ATGCACGGTC CCGCTAAGAA TACAGAAGAG GAGCAGTACA   2040
AGGTTACAAA GGCAGAGCTC GCAGAAACAG AGTACGTGTT TGACGTGGAC AAGAAGCGAT   2100
GCGTTAAGAA GGAAGAAGCC TCAGGACTTG TCCTTTCGGG AGAACTGACC AACCCGCCCT   2160
ATCACGAACT AGCTCTTGAG GGACTGAAGA CTCGACCCGC GGTCCCGTAC AAGGTTGAAA   2220
CAATAGGAGT GATAGGCACA CCAGGATCGG GCAAGTCAGC TATCATCAAG TCAACTGTCA   2280
CGGCACGTGA TCTTGTTACC AGCGGAAAGA AAGAAAACTG CCGCGAAATT GAGGCCGACG   2340
TGCTACGGCT GAGGGGCATG CAGATCACGT CGAAGACAGT GGATTCGGTT ATGCTCAACG   2400
GATGCCACAA AGCCGTAGAA GTGCTGTATG TTGACGAAGC GTTCCGGTGC CACGCAGGAG   2460
CACTACTTGC CTTGATTGCA ATCGTCAGAC CCCGTAAGAA GGTAGTACTA TGCGGAGACC   2520
CTAAGCAATG CGGATTCTTC AACATGATGC AACTAAAGGT ACATTTCAAC CACCCTGAAA   2580
AAGACATATG TACCAAGACA TTCTACAAGT TTATCTCCCG ACGTTGCACA CAGCCAGTCA   2640
CGGCTATTGT ATCGACACTG CATTACGATG GAAAATGAA AACCACAAAC CGTGCAAGA    2700
AGAACATCGA AATCGACATT ACAGGGGCCA CGAAGCCGAA GCCAGGGGAC ATCATCCTGA   2760
CATGTTTCCG CGGGTGGGTT AAGCAACTGC AAATCGACTA TCCCGGACAT GAGGTAATGA   2820
CAGCCGCGGC CTCACAAGGG CTAACCAGAA AAGGAGTATA TGCCGTCCGG CAAAAAGTCA   2880
ATGAAAACCC GCTGTACGCG ATCACATCAG AGCATGTGAA CGTGTTGCTC ACCCGCACTG   2940
AGGACAGGCT AGTATGGAAA ACTTTACAGG GCGACCCATG GATTAAGCAG CTCACTAACG   3000
TACCTAAAGG AAATTTTCAG GCCACCATCG AGGACTGGGA AGCTGAACAC AAGGGAATAA   3060
```

```
TTGCTGCGAT   AAACAGTCCC   GCTCCCCGTA   CCAATCCGTT   CAGCTGCAAG   ACTAACGTTT     3120
GCTGGGCGAA   AGCACTGGAA   CCGATACTGG   CCACGGCCGG   TATCGTACTT   ACCGGTTGCC     3180
AGTGGAGCGA   GCTGTTCCCA   CAGTTTGCGG   ATGACAAACC   ACACTCGGCC   ATCTACGCCT     3240
TAGACGTAAT   TTGCATTAAG   TTTTTCGGCA   TGGACTTGAC   AAGCGGGCTG   TTTTCCAAAC     3300
AGAGCATCCC   GTTAACGTAC   CATCCTGCCG   ACTCAGCGAG   GCCAGTAGCT   CATTGGGACA     3360
ACAGCCCAGG   AACACGCAAG   TATGGGTACG   ATCACGCCGT   TGCCGCCGAA   CTCTCCCGTA     3420
GATTTCCGGT   GTTCCAGCTA   GCTGGGAAAG   GCACACAGCT   TGATTTGCAG   ACGGGCAGAA     3480
CTAGAGTTAT   CTCTGCACAG   CATAACTTGG   TCCCAGTGAA   CCGCAATCTC   CCTCACGCCT     3540
TAGTCCCCGA   GCACAAGGAG   AAACAACCCG   GCCCGGTCGA   AAAATTCTTG   AGCCAGTTCA     3600
AACACCACTC   CGTACTTGTG   ATCTCAGAGA   AAAAAATTGA   AGCTCCCCAC   AAGAGAATCG     3660
AATGGATCGC   CCCGATTGGC   ATAGCCGGCG   CAGATAAGAA   CTACAACCTG   GCTTTCGGGT     3720
TTCCGCCGCA   GGCACGGTAC   GACCTGGTGT   TCATCAATAT   TGGAACTAAA   TACAGAAACC     3780
ATCACTTTCA   ACAGTGCGAA   GACCACGCGG   CGACCTTGAA   AACCCTTTCG   CGTTCGGCCC     3840
TGAACTGCCT   TAACCCCGGA   GGCACCCTCG   TGGTGAAGTC   CTACGGTTAC   GCCGACCGCA     3900
ATAGTGAGGA   CGTAGTCACC   GCTCTTGCCA   GAAAATTTGT   CAGAGTGTCT   GCAGCGAGGC     3960
CAGAGTGCGT   CTCAAGCAAT   ACAGAAATGT   ACCTGATTTT   CCGACAACTA   GACAACAGCC     4020
GCACACGACA   ATTCACCCCG   CATCATTTGA   ATTGTGTGAT   TCGTCCGTG    TACGAGGGTA     4080
CAAGAGACGG   AGTTGGAGCC   GCACCGTCGT   ACCGTACTAA   AAGGGAGAAC   ATTGCTGATT     4140
GTCAAGAGGA   AGCAGTTGTC   AATGCAGCCA   ATCCACTGGG   CAGACCAGGA   GAAGGAGTCT     4200
GCCGTGCCAT   CTATAAACGT   TGGCCGAACA   GTTTCACCGA   TTCAGCCACA   GAGACAGGTA     4260
CCGCAAAACT   GACTGTGTGC   CAAGGAAAGA   AAGTGATCCA   CGCGGTTGGC   CCTGATTTCC     4320
GGAAACACCC   AGAGGCAGAA   GCCCTGAAAT   TGCTGCAAAA   CGCCTACCAT   GCAGTGGCAG     4380
ACTTAGTAAA   TGAACATAAT   ATCAAGTCTG   TCGCCATCCC   ACTGCTATCT   ACAGGCATTT     4440
ACGCAGCCGG   AAAAGACCGC   CTTGAGGTAT   CACTTAACTG   CTTGACAACC   GCGCTAGACA     4500
GAACTGATGC   GGACGTAACC   ATCTACTGCC   TGGATAAGAA   GTGGAAGGAA   AGAATCGACG     4560
CGGTGCTCCA   ACTTAAGGAG   TCTGTAACTG   AGCTGAAGGA   TGAGGATATG   GAGATCGACG     4620
ACGAGTTAGT   ATGGATCCAT   CCGGACAGTT   GCCTGAAGGG   AAGAAAGGGA   TTCAGTACTA     4680
CAAAAGGAAA   GTTGTATTCG   TACTTTGAAG   GCACCAAATT   CCATCAAGCA   GCAAAAGATA     4740
TGGCGGAGAT   AAAGGTCCTG   TTCCCAAATG   ACCAGGAAAG   CAACGAACAA   CTGTGTGCCT     4800
ACATATTGGG   GGAGACCATG   GAAGCAATCC   GCGAAAAATG   CCCGGTCGAC   CACAACCCGT     4860
CGTCTAGCCC   GCCAAAAACG   CTGCCGTGCC   TCTGTATGTA   TGCCATGACG   CCAGAAAGGG     4920
TCCACAGACT   CAGAAGCAAT   AACGTCAAAG   AAGTTACAGT   ATGCTCCTCC   ACCCCCTTC     4980
CAAAGTACAA   AATCAAGAAT   GTTCAGAAGG   TTCAGTGCAC   AAAAGTAGTC   CTGTTTAACC     5040
CGCATACCCC   CGCATTCGTT   CCCGCCCGTA   AGTACATAGA   AGCACCAGAA   CAGCCTGCAG     5100
CTCCGCCTGC   ACAGGCCGAG   GAGGCCCCCG   GAGTTGTAGC   GACACCAACA   CCACCTGCAG     5160
CTGATAACAC   CTCGCTTGAT   GTCACGGACA   TCTCACTGGA   CATGGAAGAC   AGTAGCGAAG     5220
GCTCACTCTT   TTCGAGCTTT   AGCGGATCGG   ACAACTACCG   AAGGCAGGTG   GTGGTGGCTG     5280
ACGTCCATGC   CGTCCAAGAG   CCTGCCCCTG   TTCCACCGCC   AAGGCTAAAG   AAGATGGCCC     5340
GCCTGGCAGC   GGCAAGAATG   CAGGAAGAGC   CAACTCCACC   GGCAAGCACC   AGCTCTGCGG     5400
ACGAGTCCCT   TCACCTTTCT   TTTGATGGGG   TATCTATATC   CTTCGGATCC   CTTTTCGACG     5460
```

```
GAGAGATGGC CCGCTTGGCA GCGGCACAAC CCCCGGCAAG TACATGCCCT ACGGATGTGC    5520
CTATGTCTTT CGGATCGTTT TCCGACGGAG AGATTGAGGA GTTGAGCCGC AGAGTAACCG    5580
AGTCGGAGCC CGTCCTGTTT GGGTCATTTG AACCGGGCGA AGTGAACTCA ATTATATCGT    5640
CCCGATCAGC CGTATCTTTT CCACCACGCA AGCAGAGACG TAGACGCAGG AGCAGGAGGA    5700
CCGAATACTG TCTAACCGGG GTAGGTGGGT ACATATTTTC GACGGACACA GGCCCTGGGC    5760
ACTTGCAAAA GAAGTCCGTT CTGCAGAACC AGCTTACAGA ACCGACCTTG GAGCGCAATG    5820
TTCTGGAAAG AATCTACGCC CCGGTGCTCG ACACGTCGAA AGAGGAACAG CTCAAACTCA    5880
GGTACCAGAT GATGCCCACC GAAGCCAACA AAAGCAGGTA CCAGTCTCGA AAAGTAGAAA    5940
ACCAGAAAGC CATAACCACT GAGCGACTGC TTTCAGGGCT ACGACTGTAT AACTCTGCCA    6000
CAGATCAGCC AGAATGCTAT AAGATCACCT ACCCGAAACC ATCGTATTCC AGCAGTGTAC    6060
CAGCGAACTA CTCTGACCCA AGTTTGCTG TAGCTGTTTG TAACAACTAT CTGCATGAGA    6120
ATTACCCGAC GGTAGCATCT TATCAGATCA CCGACGAGTA CGATGCTTAC TTGGATATGG    6180
TAGACGGGAC AGTCGCTTGC CTAGATACTG CAACTTTTTG CCCCGCCAAG CTTAGAAGTT    6240
ACCCGAAAAG ACACGAGTAT AGAGCCCCAA ACATCCGCAG TGCGGTTCCA TCAGCGATGC    6300
AGAACACGTT GCAAAACGTG CTCATTGCCG CGACTAAAAG AAACTGCAAC GTCACACAAA    6360
TGCGTGAACT GCCAACACTG GACTCAGCGA CATTCAACGT TGAATGCTTT CGAAAATATG    6420
CATGCAATGA CGAGTATTGG GAGGAGTTTG CCCGAAAGCC AATTAGGATC ACTACTGAGT    6480
TCGTTACCGC ATACGTGGCC AGACTGAAAG GCCCTAAGGC CGCCGCACTG TTCGCAAAGA    6540
CGCATAATTT GGTCCCATTG CAAGAAGTGC CTATGGATAG ATTCGTCATG GACATGAAAA    6600
GAGACGTGAA AGTTACACCT GGCACGAAAC ACACAGAAGA AAGACCGAAA GTACAAGTGA    6660
TACAAGCCGC AGAACCCCTG GCGACCGCTT ACCTATGCGG GATCCACCGG GAGTTAGTGC    6720
GCAGGCTTAC AGCCGTTTTG CTACCCAACA TTCACACGCT CTTTGACATG TCGGCGGAGG    6780
ACTTTGATGC AATCATAGCA GAACACTTCA AGCAAGGTGA CCCGGTACTG GAGACGGATA    6840
TCGCCTCGTT CGACAAAAGC CAAGACGACG CTATGGCGTT AACCGGCCTG ATGATCTTGG    6900
AAGACCTGGG TGTGGACCAA CCACTACTCG ACTTGATCGA GTGCGCCTTT GGAGAAATAT    6960
CATCCACCCA TCTGCCCACG GGTACCCGTT TCAAATTCGG GGCGATGATG AAATCCGGAA    7020
TGTTCCTCAC GCTCTTTGTC AACACAGTTC TGAATGTCGT TATCGCCAGC AGAGTATTGG    7080
AGGAGCGGCT TAAAACGTCC AAATGTGCAG CATTTATCGG CGACGACAAC ATTATACACG    7140
GAGTAGTATC TGACAAAGAA ATGGCTGAGA GGTGTGCCAC CTGGCTCAAC ATGGAGGTTA    7200
AGATCATTGA CGCAGTCATC GGCGAGAGAC CACCTTACTT CTGCGGTGGA TTCATCTTGC    7260
AAGATTCGGT TACCTCCACA GCGTGTCGCG TGGCGGACCC CTTGAAAAGG CTGTTTAAGT    7320
TGGGTAAACC GCTCCCAGCC GACGATGAGC AAGACGAAGA CAGAAGACGC GCTCTGCTAG    7380
ATGAAACAAA GGCGTGGTTT AGAGTAGGTA TAACAGACAC CTTAGCAGTG GCCGTGGCAA    7440
CTCGGTATGA GGTAGACAAC ATCACCTG TCCTGCTGGC ATTGAGAACT TTTGCCCAGA    7500
GCAAAAGAGC ATTTCAAGCC ATCAGAGGGG AAATAAAGCA TCTCTACGGT GGTCCTAAAT    7560
AGTCAGCATA GTACATTTCA TCTGACTAAT ACCACAACAC CACCACCATG AATAGAGGAT    7620
TCTTTAACAT GCTCGGCCGC CGCCCCTTCC CAGCCCCCAC TGCCATGTGG AGGCCGCGGA    7680
GAAGGAGGCA GGCGGCCCCG ATGCCTGCCC GCAATGGGCT GGCTTCCCAA ATCCAGCAAC    7740
TGACCACAGC CGTCAGTGCC CTAGTCATTG ACAGGCAAC TAGACCTCAA ACCCCACGCC    7800
CACGCCCGCC GCCGCGCCAG AAGAAGCAGG CGCCAAAGCA ACCACCGAAG CCGAAGAAAC    7860
```

```
CAAAAACACA GGAGAAGAAG AAGAAGCAAC CTGCAAAACC CAAACCCGGA AAGAGACAGC    7920
GTATGGCACT TAAGTTGGAG GCCGACAGAC TGTTCGACGT CAAAAATGAG GACGGAGATG    7980
TCATCGGGCA CGCACTGGCC ATGGAAGGAA AGGTAATGAA ACCACTCCAC GTGAAAGGAA    8040
CTATTGACCA CCCTGTGCTA TCAAAGCTCA AATTCACCAA GTCGTCAGCA TACGACATGG    8100
AGTTCGCACA GTTGCCGGTC AACATGAGAA GTGAGGCGTT CACCTACACC AGTGAACACC    8160
CTGAAGGGTT CTACAACTGG CACCACGGAG CGGTGCAGTA TAGTGGAGGC AGATTTACCA    8220
TCCCCCGCGG AGTAGGAGGC AGAGGAGACA GTGGTCGTCC GATTATGGAT AACTCAGGCC    8280
GGGTTGTCGC GATAGTCCTC GGAGGGGCTG ATGAGGGAAC AAGAACCGCC CTTTCGGTCG    8340
TCACCTGGAA TAGCAAAGGG AAGACAATCA AGACAACCCC GGAAGGGACA GAAGAGTGGT    8400
CTGCTGCACC ACTGGTCACG GCCATGTGCT TGCTTGGAAA CGTGAGCTTC CCATGCAATC    8460
GCCCGCCCAC ATGCTACACC CGCGAACCAT CCAGAGCTCT CGACATCCTC GAAGAGAACG    8520
TGAACCACGA GGCCTACGAC ACCCTGCTCA ACGCCATATT GCGGTGCGGA TCGTCCGGCA    8580
GAAGTAAAAG AAGCGTCACT GACGACTTTA CCTTGACCAG CCCGTACTTG GGCACATGCT    8640
CGTACTGTCA CCATACTGAA CCGTGCTTTA GCCCGATTAA GATCGAGCAG GTCTGGGATG    8700
AAGCGGACGA CAACACCATA CGCATACAGA CTTCCGCCCA GTTTGGATAC GACCAAAGCG    8760
GAGCAGCAAG CTCAAATAAG TACCGCTACA TGTCGCTCGA GCAGGATCAT ACTGTCAAAG    8820
AAGGCACCAT GGATGACATC AAGATCAGCA CCTCAGGACC GTGTAGAAGG CTTAGCTACA    8880
AAGGATACTT TCTCCTCGCG AAGTGTCCTC CAGGGGACAG CGTAACGGTT AGCATAGCGA    8940
GTAGCAACTC AGCAACGTCA TGCACAATGG CCCGCAAGAT AAAACCAAAA TTCGTGGGAC    9000
GGGAAAAATA TGACCTACCT CCCGTTCACG GTAAGAAGAT TCCTTGCACA GTGTACGACC    9060
GTCTGAAAGA AACAACCGCC GGCTACATCA CTATGCACAG GCCGGGACCG CATGCCTATA    9120
CATCCTATCT GGAGGAATCA TCAGGGAAAG TTTACGCGAA GCCACCATCC GGGAAGAACA    9180
TTACGTACGA GTGCAAGTGC GGCGATTACA AGACCGGAAC CGTTACGACC CGTACCGAAA    9240
TCACGGGCTG CACCGCCATC AAGCAGTGCG TCGCCTATAA GAGCGACCAA ACGAAGTGGG    9300
TCTTCAACTC GCCGGACTCG ATCAGACACG CCGACCACAC GGCCCAAGGG AAATTGCATT    9360
TGCCTTTCAA GCTGATCCCG AGTACCTGCA TGGTCCCTGT TGCCCACGCG CCGAACGTAG    9420
TACACGGCTT TAAACACATC AGCCTCCAAT TAGACACAGA CCATCTGACA TTGCTCACCA    9480
CCAGGAGACT AGGGGCAAAC CCGGAACCAA CCACTGAATG GATCATCGGA AACACGGTTA    9540
GAAACTTCAC CGTCGACCGA GATGGCCTGG AATACATATG GGGCAATCAC GAACCAGTAA    9600
GGGTCTATGC CCAAGAGTCT GCACCAGGAG ACCCTCACGG ATGGCCACAC GAAATAGTAC    9660
AGCATTACTA TCATCGCCAT CCTGTGTACA CCATCTTAGC CGTCGCATCA GCTGCTGTGG    9720
CGATGATGAT TGGCGTAACT GTTGCAGCAT TATGTGCCTG TAAAGCGCGC CGTGAGTGCC    9780
TGACGCCATA TGCCCTGGCC CCAAATGCCG TGATTCCAAC TTCGCTGGCA CTTTTGTGCT    9840
GTGTTAGGTC GGCTAATGCT GAAACATTCA CCGAGACCAT GAGTTACTTA TGGTCGAACA    9900
GCCAGCCGTT CTTCTGGGTC CAGCTGTGTA TACCTCTGGC CGCTGTCGTC GTTCTAATGC    9960
GCTGTTGCTC ATGCTGCCTG CCTTTTTTAG TGGTTGCCGG CGCCTACCTG GCGAAGGTAG   10020
ACGCCTACGA ACATGCGACC ACTGTTCCAA ATGTGCCACA GATACCGTAT AAGGCACTTG   10080
TTGAAAGGGC AGGGTACGCC CCGCTCAATT GGAGATTAC  TGTCATGTCC TCGGAGGTTT   10140
TGCCTTCCAC CAACCAAGAG TACATTACCT GCAAATTCAC CACTGTGGTC CCCTCCCCTA   10200
AAGTCAGATG CTGCGGCTCC TTGGAATGTC AGCCCGCCGC TCACGCAGAC TATACCTGCA   10260
```

| | | | | | | |
|---|---|---|---|---|---|---|
| AGGTCTTTGG | AGGGGTGTAC | CCCTTCATGT | GGGGAGGAGC | ACAATGTTTT | TGCGACAGTG | 10320 |
| AGAACAGCCA | GATGAGTGAG | GCGTACGTCG | AATTGTCAGT | AGATTGCGCG | ACTGACCACG | 10380 |
| CGCAGGCGAT | TAAGGTGCAT | ACTGCCGCGA | TGAAAGTAGG | ACTGCGTATA | GTGTACGGGA | 10440 |
| ACACTACCAG | TTTCCTAGAT | GTGTACGTGA | ACGGAGTCAC | ACCAGGAACG | TCTAAAGACC | 10500 |
| TGAAAGTCAT | AGCTGGACCA | ATTTCAGCAT | TGTTTACACC | ATTCGATCAC | AAGGTCGTTA | 10560 |
| TCAATCGCGG | CCTGGTGTAC | AACTATGACT | TTCCGGAATA | CGGAGCGATG | AAACCAGGAG | 10620 |
| CGTTTGGAGA | CATTCAAGCT | ACCTCCTTGA | CTAGCAAAGA | CCTCATCGCC | AGCACAGACA | 10680 |
| TTAGGCTACT | CAAGCCTTCC | GCCAAGAACG | TGCATGTCCC | GTACACGCAG | GCCGCATCTG | 10740 |
| GATTCGAGAT | GTGGAAAAAC | AACTCAGGCC | GCCCACTGCA | GGAAACCGCC | CCTTTGGGT | 10800 |
| GCAAGATTGC | AGTCAATCCG | CTTCGAGCGG | TGGACTGCTC | ATACGGGAAC | ATTCCATTT | 10860 |
| CTATTGACAT | CCCGAACGCT | GCCTTTATCA | GGACATCAGA | TGCACCACTG | GTCTCAACAG | 10920 |
| TCAAATGTGA | TGTCAGTGAG | TGCACTTATT | CAGCGGACTT | CGGAGGGATG | GCTACCCTGC | 10980 |
| AGTATGTATC | CGACCGCGAA | GGACAATGCC | CTGTACATTC | GCATTCGAGC | ACAGCAACCC | 11040 |
| TCCAAGAGTC | GACAGTTCAT | GTCCTGGAGA | AAGGAGCGGT | GACAGTACAC | TTCAGCACCG | 11100 |
| CGAGCCCACA | GGCGAACTTC | ATTGTATCGC | TGTGTGGTAA | GAAGACAACA | TGCAATGCAG | 11160 |
| AATGCAAACC | ACCAGCTGAT | CATATCGTGA | GCACCCCGCA | CAAAAATGAC | CAAGAATTCC | 11220 |
| AAGCCGCCAT | CTCAAAAACT | TCATGGAGTT | GGCTGTTTGC | CCTTTCGGC | GGCGCCTCGT | 11280 |
| CGCTATTAAT | TATAGGACTT | ATGATTTTG | CTTGCAGCAT | GATGCTGACT | AGCACACGAA | 11340 |
| GATGACCGCT | ACGCCCCAAT | GACCCGACCA | GCAAAACTCG | ATGTACTTCC | GAGGAACTGA | 11400 |
| TGTGCATAAT | GCATCAGGCT | GGTATATTAG | ATCCCCGCTT | ACCGCGGGCA | ATATAGCAAC | 11460 |
| ACCAAAACTC | GACGTATTTC | CGAGGAAGCG | CAGTGCATAA | TGCTGCGCAG | TGTTGCCAAA | 11520 |
| TAATCACTAT | ATTAACCATT | TATTCAGCGG | ACGCCAAAAC | TCAATGTATT | TCTGAGGAAG | 11580 |
| CATGGTGCAT | AATGCCATGC | AGCGTCTGCA | TAACTTTTA | TTATTTCTTT | TATTAATCAA | 11640 |
| CAAAATTTTG | TTTTTAACAT | TTC | | | | 11663 |

CDNA CLONE FOR SOUTH AFRICAN ARBOVIRUS NO. 86

This invention was made with government support under Grant No. 2-ROIA122186 (09-13) awarded by the National Institutes of Health. The government has certain rights in the invention.

FIELD OF THE INVENTION

The present invention relates to live attenuated vaccines in general, and particularly relates to attenuated vaccines produced from South African Arbovirus No. 86 (S.A.AR86) virus.

BACKGROUND OF THE INVENTION

South African Arbovirus No. 86 (S.A.AR86) is a synthetic isolate of Sindbis virus. S.A.AR 86 was originally isolated from mosquitoes. The virus is antigenically related to Sindbis virus and to two other arbovirus isolates, Girdwood and Ockelbo82. See, Malherbe et al., *South African Medical Journal*, 37:547 (1963) and Niklasson et al., *Am. J. Trop. Med. Hyg.* 33:1212 (1984), respectively. The latter is associated with a human disease, also known as Ockelbo. Sindbis virus is the prototype member of the alphavirus genus of the Togaviridae. The Sindbis virus includes various stains, including S.A.AR86 and Sindbis AR339. The genome of the Sindbis virus is a single strand of RNA which contains the information for the viral genes, and which is infectious when introduced into the cytoplasm of cells.

Full-length cDNA clones of positive-strand RNA viruses are important tools for the study of the biology of viruses including Sindbis viruses. It is known with respect to several viral systems that in vitro transcripts of cDNA clones, and in some cases the cDNA itself, can initiate a complete and productive infectious cycle upon introduction into susceptible cells. See Racaniello et al., *Science* 214:916 (1981); Ahlquist et al., *Proc. Natl. Acad. Sci. USA* 81:7066 (1984); Kaplan et al., *Proc. Natl. Acad. Sci. USA* 82:8424 (1985); Mizutani et al., *J. Virol.* 56:628 (1985); van der Werf, *Proc. Natl. Acad. Sci. USA* 83:2330 (1986); Rice et al., *J. Virol.* 61:3809 (1987); and Vos et al., *Virology* 165:33 (1988). This has made it possible to test progeny virus for phenotypic manifestations of directed mutations and recombinations which have been introduced into the cDNA clone. Pathogenesis studies with several positive-strand viruses, including the picornaviruses and the alphaviruses have been advanced significantly by the use of full-length cDNA clones.

As another useful application, live attenuated viral vaccines may be produced using full-length cDNA clones. Live attenuated viral vaccines are among the most successful means of controlling viral disease. However for some virus pathogens, immunization with a live virus strain may be either impractical or unsafe. Sindbis virus is subclinical in humans, but is closely related to other viruses which do induce clinical diseases in humans, such as Ockelbo, an epidemic polyarthritis syndrome common in areas of Scandinavia and Northern Europe. Accordingly, Sindbis virus vaccines are desirable for producing an immunogenic response to such clinical diseases. Sindbis virus vaccines are also desirable as viral carriers in virus constructs which express genes encoding immunizing antigens for other viruses. See U.S. Pat. No. 5,217,879 to Huang et al. Huang et al. '879 describes sindbis infectious viral vectors. However, the reference does not describe the cDNA sequence of S.A.AR86 virus, or clones or viral vectors produced therefrom.

Accordingly, there remains a need in the art for full-length cDNA clones of positive-strand RNA viruses, such as the S.A.AR86 strain of Sindbis. In addition, there is a need in the art for full-length cDNA clones of S.A.AR86 encoding infectious RNA transcripts. Further, there remains a need in the art for cDNA clones of S.A.AR86 which encode RNA transcripts which may be used to produce infectious attenuated viral particles, and methods of producing such viral particles.

SUMMARY OF THE INVENTION

As a first aspect, the present invention provides a recombinant DNA comprising a cDNA coding for an infectious South African Arbovirus No. 86 (S.A.AR86) virus RNA transcript and a heterologous promoter positioned upstream from the cDNA and operatively associated therewith. The cDNA is selected from the group consisting of (i) cDNA having the sequence given herein as SEQ ID NO.: 1, (ii) cDNA having the same RNA coding sequence as the cDNA given herein as SEQ ID NO.: 1, and (iii) cDNA according to (i) or (ii) above and further containing at least one attenuating mutation. Preferably at least one attenuating mutation is included in the cDNA, and more preferably at least two attenuating mutations are included in the cDNA. Attenuating mutations may, for example, be provided in any of the nsP1, E2, and nsP2 coding regions of the cDNA. Preferably at least one silent mutation is included in the cDNA in addition to the attenuating mutation(s).

As a second aspect, the present invention provides an infectious RNA transcript encoded by the cDNA.

As a third aspect, the present invention provides infectious attenuated viral particles containing the RNA transcript encoded by the cDNA.

The foregoing and other aspects of the present invention are explained in detail in the detailed description set forth below.

DETAILED DESCRIPTION OF THE INVENTION

Figure 1:
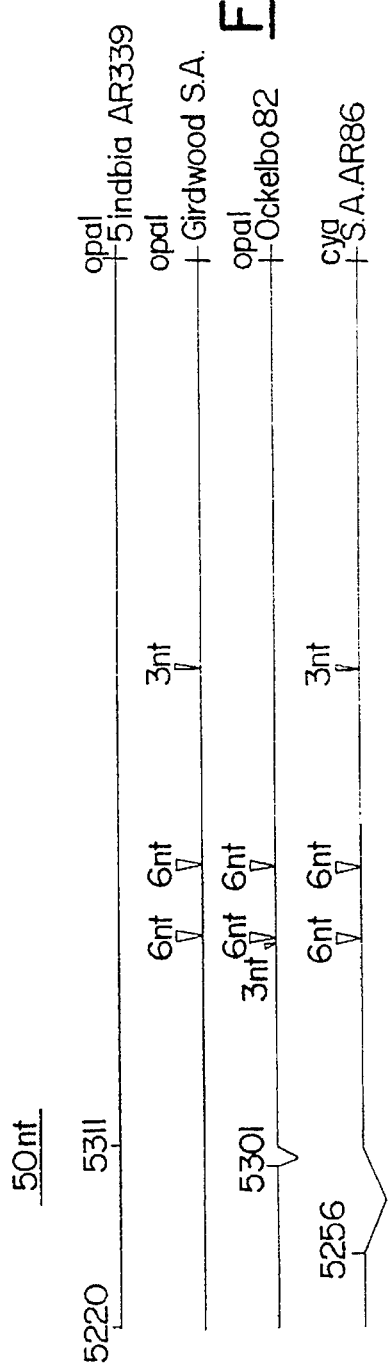
FIG. 1 shows the relationship of the 3' half of the nsP3 gene among various Sindbis-like isolates.

The South African Arbovirus No. 86 (S.A.AR86) viral clones employed in practicing the present invention are genomic clones which code for an RNA transcript, which RNA trasncript is capable of producing live encapsidated S.A.AR86 virus when used to transfect a S.A.AR86 virus-permissive cell.

S.A.AR86 virus-permissive cells are cells which, upon transfection with the vital RNA transcript, are capable of producing vital particles. The S.A.AR86 virus has a broad host cell range. Examples of suitable host cells include, but are not limited to Veto cells, baby hamster kidney (BHK) cells, and chicken embryo fibroblast cells. Uptake of the RNA into the cells can be achieved by any suitable means, such as for example, by treating the cells with DEAE-dextran, treating the cells with "LIPOFECTIN", and by electroporesis, with electroporesis being the currently preferred means of achieving RNA uptake into the host cells.

The phrases "attenuating mutation" and "attenuating amino acid," as used herein, mean a nucleotide mutation or an amino acid coded for in view of such a mutation which result in a decreased probability of causing disease in its host (i.e., a loss of virulence), in accordance with standard terminology in the art. See, e.g., B. Davis, et al., *Microbiology* 132 (3d ed. 1980), whether the mutation be a substitution mutation or an in-frame deletion mutation. The phrase "attenuating mutation" excludes mutations which would be lethal to the virus.

The phrase "silent mutation" as used herein refers to mutations in the cDNA coding sequence which do not produce mutations in the corresponding RNA sequence transcribed therefrom.

The cDNA clone has a sequence as given herein as SEQ ID NO.: 1. Alternatively, the cDNA clone may have a sequence which differs from the cDNA of SEQ ID NO.: 1, but which has the same RNA coding sequence as the cDNA given herein as SEQ ID NO.: 1. Thus, the cDNA clone may include one or more silent mutations. For example, the clone sequence may differ from the wild-type S.A.AR86 sequence given herein as SEQ ID NO.: 1, by the inclusion of silent mutations at any or all of nucleotides 215, 3863, 4196, 4295, 5972, and 9113. The silent mutations at the foregoing nucleotides may be substitution or inframe deletion mutations, such as for example, the substitution of guanine for adenine at nucleotide 215 of the cDNA sequence given herein as SEQ ID NO.: 1; or the substitution of guanine for cytosine at nucleotide 3863 of the cDNA sequence given herein as SEQ ID NO.: 1; or the substitution of adenine for thymine at nucleotide 4196 of the cDNA sequence given herein as SEQ ID NO.: 1; or the substitution of thymine for cytosine at nucleotide 4295 of the cDNA sequence given herein as SEQ ID NO.: 1; or the substitution of guanine for thymine at nucleotide 5972 of the cDNA sequence given herein as SEQ ID NO.: 1; or the substitution of cytosine for thymine at nucleotide 9113 of the cDNA sequence given herein as SEQ ID NO.: 1. In yet another emobidment, the cDNA clone has a sequence according to either of the foregoing described sequences, but which also includes attenuating mutations. The attenuating mutations being described more fully hereinafter.

Promoter sequnces and S.A.AR86 virus cDNA clones are operatively associated in the present invention such that the promoter causes the cDNA clone to be transcribed in the presence of an RNA polymerase which binds to the promoter. The promoter is positioned on the 5' end (with respect to the virion RNA sequence), or "upstream" from, the cDNA clone. An excessive number of nucleotides between the promoter sequence and the cDNA clone will result in the inoperability of the construct. Hence, the number of nucleotides between the promoter seuqence and the cDNA clone is preferably not more than eight, more preferably not more than five, still more preferably not more than three, and most preferably not more than one. Examples of promoters which are useful in the cDNA sequences of the present invention include, but are not limited to T3 promoters, T7 promoters, and SP6 promoters. The DNA sequence of the present invention may reside in any suitable transcription vector. The DNA sequence preferably has a complementary DNA sequence bonded therto so that the double-stranded sequence will serve as an active template for RNA polymerase. The transcription vector preferably comprises a plasmid. When the DNA sequence comprises a plasmid, it is preferred that a unique restriction site be provided 3' (with respect to the virion RNA sequence) to (i.e., "downstream" from) the cDNA clone. This provides a means for linearizing the DNA sequence to enhance the efficiency of transcription of genome-length RNA in vitro.

The cDNA clone can be generated by any of a variety of suitable methods known to those skilled in the art. A preferred method is the method set forth in U.S. Pat. No. 5,185,440 to Davis et al., and Gubler et al., Gene 25:263 (1983), the disclosures of which are incorporated herein by reference in their entirety. Attenuating mutations of S.A.AR86 are identified by sequenceing attenuated strains of the S.A.AR86 virus and comparing the sequence of the attenuated strain with the sequence of the corresponding wild-type virus. Serial passage techniques for the generation of attenuated strains may be carreid out in accordance with known procedures. Preferably, the atenuated strains are generated by selecting strains at each passage during serial passage in cell culture which either grow rapidly or penetrate the cell more rapidly. This selection process, which reduces the number of serial passages required to obtain attenuated strains, is known. See, e.g., Olmstead et al., *Science* 225:424 (1984); and Johnston et al., *Virology* 162:437 (1988). the disclosures of which are incorporated herein by reference in their entirety. cDNA clones may be modified to incorporate attenuating mutations by site-directed mutagenesis in accordance with known procedures. An exemplary technique is that of Kunkel *Proc. Natl. Acad. Sci.* (USA) 82:488 (1985). These same techniques may be used to join the heterologous promoter to the cDNA clone.

RNA is preferably synthesized from the DNA sequence in vitro using purified RNA polymerase in the presence of ribonucleotide triphosphates in accordance with conventional techniques.

Pharmaceutical compositions, such as vaccines, containing the S.A.AR86 clone of the present invention comprise an immunogenic amount of a live attenutated virus as disclosed herein in combination with a pharmaceutically acceptable carrier. An "effective immunogenic amount" is an amount of the attenuated virus sufficient to evoke an immune response in the subject to which the vaccine is administered. An amount of from about $10^1$ to about $10^5$ plaque forming units per dose is believed to be suitable, depending upon the age and specieis of the subject being treated. Examples of suitable pharmaceutically acceptable carriers include, but are not limited to, sterile pyrogen-free water and sterile pyrogen-free physiological saline solution. Subjects which may be administered immunogenic amounts of the live attenuated viruses of the present invention include both human and animal (e.g., horse, donkey, mouse, hamster, monkeys) subjects. Administration may be by an suitable means, such as intraperitoneoal, intracerebral or intramuscular injection.

Complimentary DNA clones of the S.A.AR86 virus are made in accordance with the procedures described herein, as supplemented with procedures known in the art. We employed as a staffing material, the S.A.AR86 virus.

A first exemplary attenuating substitution mutation in a S.A.AR86 clone useful in practicing the present invention is a substitution mutation which codes for an attenuating amino acid, preferably isoleucine as nsP1 amino acid 538.

A second exemplary attenuating subsitution mutation in a S.A.AR86 clone useful in practicing the present invention is a substitution mutation which codes for an attenuating amino acid, preferably threonine as E2 amino acid 304.

A third exemplary attenuating subsitution mutation in a S.A.AR86 clone useful in practicing the present invention is a substitution mutation which codes for an attenuating amino acid, preferably lysine as E2 amino acid 314.

A fourth exemplary attenuating subsitution mutation in a S.A.AR86 clone useful in practicing the present invention is a substitution mutation which codes for an attenuating amino acid, preferably alanine as E2 amino acid 376.

A fifth exemplary attenuating substitution mutation in a S.A.AR86 clone useful in practicing the present invention is a substitution mutation which codes for an attenuating amino acid, preferably leucine as E2 amino acid 378.

A sixth exemplary attenuating subsitution mutation in a S.A.AR86 clone useful in practicing the present invention is a substitution mutation which codes for an attenuating amino acid, preferably glycine as nsP2 amino acid 96.

A seventh exemplary attenuating substitution mutation in a S.A.AR86 clone useful in practicing the present invention is a substitution mutation which codes for an attenuating amino acid, preferably valine as nsP2 amino acid 372.

The cDNA clones according to the present invention are useful for the preparation of pharmaceutical formulations, such as vaccines, as described above. In addition, the cDNA clones of the present invention are useful for administration to animals for the purpose of producing antibodies to the S.A.AR86 virus, which antibodies may be collected and used in known diagnostic techniques for the detection of S.A.AR86 virus.

The following examples are provided to illustrate the present invention, and should not be construed as limiting thereof. In these examples, nt means nucleotide.

EXAMPLE 1

Relationship of S.A.AR86 Clone to Other Sindbis Strains

At the nucleotide level, S.A.AR86 differs from the sequence of Sindbis strain AR339 by 688 nucleotides (111 amino acids). From the published Sindbis sequence (See, Strauss et al., *Virol.* 133:92 (1984)), S.A.AR86 differs by 704 nucleotides and 119 amino acids. S.A.AR86 differs from the sequence of Ockelbo82 (See, Shirako et al., *Virol* 182:753 (1991)) by 430 nucleotides (67 amino acids). Included in these differences are several insertions and deletions present in S.A.AR86 relative to the Sindbis sequences The relationship of the 3' half of the nsP3 gene among various Sindbis-like isolates is shown in FIG. 1.

EXAMPLE 2

Observed Mortality in Mice Infected with S.A.AR86

Adult mice are inoculated intracerebrally (i.c.) with low doses of S.A.AR86, and 100% motaility is observed. The methods employed for evaluating the mortality of mice are set forth in D. Russell, et al., *J. Virol.* 63(4):1619 (1989), the disclosure of which is incorporated herein by reference in its entirety. This high mortality rate is unique among "Sindbis-like" viruses which are characteristically avirulent in adult mice. Also unique in the S.A.AR86 strain is the cys substitution for the opal stop codon normally found between the nsP3 and nsP4 genes.

EXAMPLE 3

Construction of S.A.AR86 Clone

The S.A.AR86 clone is constructed by substituting partial cDNA clones of S.A.AR86 genomic RNA into pTR5000, one of a series of Sindbis AR339 cDNA clones. Construction of pTR5000 (a full-length cDNA clone of Sindbis following the SP6 phage promoter and containing mostly Sindbis AR339 sequences) is accomplished by sequential replacement of AR339-derived cDNAs into the plasmid pToto1101 background, according to the technique described in Rice et al., *J. Virol.* 61:3809 (1987). The replacement of the AR339-derived cDNAs into the plasmid pToto1101 background is shown in FIG. 2.

Production of the cDNAs used in constructing pTR5000 has been described previously in Polo et al., *J. Virol.* 62:2124 (1988), as has the construction of pTR2000, see Polo et al., *J. Virol.* 62:2124 (1988) and Polo et al., *J. Virol.* 64:4438 (1990). Nucleotide numbering follows that of Strauss et al. *Virol* 133:92 (1984).

Figure 2:
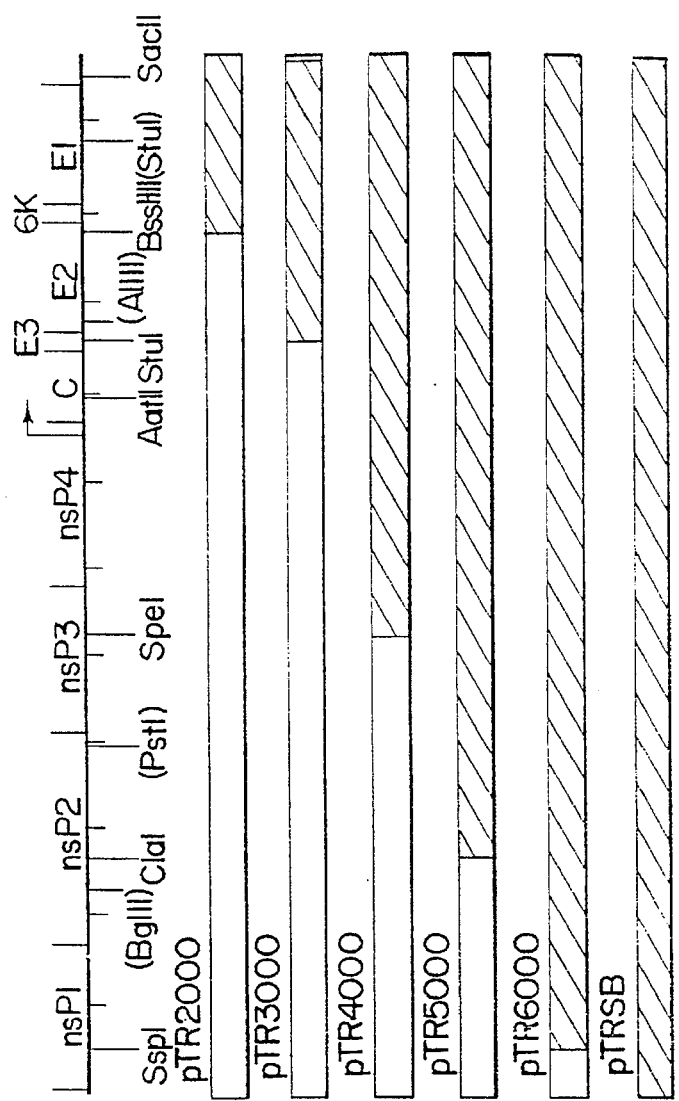
FIG. 2 shows the replacement of of the AR339-derived cDNAs into the plasmid pToto1101 background.

The StuI (nt8571) to SacII (nt11484) fragment of pToto1101 is removed and replaced with the analogous fragment from clone pSB4 to form pTR2000, using the loss of the pToto1101 StuI site at nt10770 (a site not present in AR339) as a screen, as shown in FIG. 2. The sequences of AR339 and pToto1101 are identical from nt11485 to the 3'-end (nt11703). Therefore, as shown in FIG. 2, these 3' sequences are of AR339 origin. Construction of pTR3000 is accomplished by replacement of the BssHII (nt9804) to StuI (nt8571) fragment of pSB3 into pTR2000 from which the analogous fragment had been removed. The AflII site found at nt8835 in pToto1101 but absent in AR339 is used to screen the recombinants. An AR339 fragment from pSB1, SpeI (nt5262) to BssHII, is used to replace the SpeI-BssHII fragment from pTR2000, using the AflII screen and forming pTR4000. To construct pTR500, pSB5 is subcloned into pUC119, and the PstI site at nt3953 is ablated using site-directed mutagenesis, as described in Kunkel, *Methods Enzymol.* 154:367 (1987), to change nt3950 from U to C. The ClaI (nt2713) to SpeI fragment is removed from the mutagenized subclone and for pTR5000, is used to replace the analogous fragment of pTR4000 using the ablated PstI site as a screen.

Partial cDNA clones of S.A.AR86 were obtained using classical reverse transcriptase (RT) procedures according to Polo et al., *J. Virol.* 62:2124 (1988), as well as RT-PCR protocols according to Heidner et al., *J. Virol.* 68:2683 (1994). These cDNA clones are used to replace analogous portions of the clone pTR5000, culminating in the construction of a full-length cDNA of the S.A.AR86 genomic sequence downstream of an SP6 promoter and followed by a poly (A) tract and a unique XbaI site. During the course of replacing S.A.AR86 sequences into pTR5000, it was observed that the pTR5000 nonstructural proteins are incompatible with those of S.A.AR86, so that the chimeric clones yielded transcripts which are not infectious for baby hamster kidney (BHK) cells. In addition, the restriction sites in the nonstructural region of S.A.AR86 are very different from the Sindbis AR339-based clones. The first complete S.A.AR86 clone, pS10, also failed to yield infectious transcripts.

The construction is repeated, beginning with pTR5000, using sequences derived from the same partial cDNA clones of S.A.AR86 as are used for the construction of pS10 except for nucleotides 3171 to 6410 (numbering from nucleotide 1 of the S.A.AR86 sequence), which are derived by RT-PCR of the genomic RNA. The resulting construct, pS22, gives infectious transcripts, but the virus derived therefrom is temperature-sensitive. Replacement of nucleotides 3171 to 6410 with an alternative RT-PCR derived cDNA corrected the temperature-sensitive defect, yielding clone pS24.

EXAMPLE 4

Observed Mortality in Mice Infected with S.A.AR86

Upon i.c. inoculation virus derived from pS24 is avirulent, whereas S.A.AR86 caused 100% mortality. Clearly, pS24 contains one or more mutations which are strongly attenuating. The complete sequence of pS24 is determined directly from pS24 and related clones. Comparison with the S.A.AR86 genomic RNA sequence reveals 5 mutations or clusters of mutations which are potentially associated with the avirulent phenotype of virus from pS24. These included the mutations or clusters of mutations indicated in clones pS56, pS51, and pS57, a mutation at nt1278 A-C (nsP1 407 K→Q), and a mutation at nt5972 T→G (nsP3 228 N→S). Clone pS24 is corrected by a combination of site-directed mutagenesis and replacement of specific pS24 sequences with cDNA fragments which do not contain the subject mutations. The resulting cDNA is pS55 which contains 5' and 3' untranslated sequences identical to S.A.AR86 genomic RNA, no coding differences with S.A.AR86 genomic RNA, and the 6 non-coding changes at nt 215 A-G, nt 3863 C-G, nt 4196 T-A, nt 4295 C-T, nt 5972 T-G, and nt 9113 T-C. Virus derived from pS55 is indistinguishable from native S.A.AR86 in tests of virulence in adult mice and by histopathological analysis of tissues from infected animals. These results, which are reported in Table 1 below, indicate that pS55 is a clone which accurately reflects native S.A.AR86 both in terms of coding sequence and in vivo phenotype.

The 3 mutations or clusters of mutations in clones pS56, pS51, and pS57 are placed independently into the pS55 background. Virus derived from each of these clones is highly attenuated in adult mice inoculated i.c. In clone pS53, the mutations at nucleotides 6 and 1672 are combined, and the resulting virus is avirulent in the adult mouse model. The mutations in pS61 are present in pS48, an intermediate clone constructed during the repair of pS24. The virus from pS48 produced small plaques on BHK cells. When these mutations are placed in the pS55 background, they also gave a highly attenuated phenotype.

TABLE 1

| AGE OF MICE | VIRULENCE IN MICE | | | |
|---|---|---|---|---|
| | S.A.AR86 | S55 | S56[2] | S51[3] |
| 4 to 6 Weeks Mortality | 100% | 100% | 80% | 20% |
| AST[1] | 6.36 ± 1.39 | 6.37 ± 1.4 | 9.37 ± 1.77 | 8.5 ± 0.7 |

[1]Average Survival Time in days.
[2]Virus isogenic with S55 except at nucleotide 6 (C → A).
[3]Virus isogenic with S55 except at nucleotide 1648 (C → T). This is nsP1 amino acid 538 (T → I).
The isoleucine is the amino acid found in all other Sindbis isolates sequenced to date.

The foregoing is illustrative of the present invention and is not to be construed as limiting thereof. The invention is defined by the following claims, with equivalents of the claims to be included therein.

That which is claimed is:

1. A recombinant DNA comprising a cDNA coding for an infectious South African Arbovirus No. 86 (S.A.AR86) virus RNA transcript, and a heterologous promoter positioned upstream from said cDNA and operatively associated therewith.

2. The recombinant DNA according to claim 1, wherein said cDNA is selected from the group consisting of (i) cDNA having the sequence of SEQ ID NO.: 1, (ii) cDNA encoding the same amino acid sequence encoded by the cDNA of SEQ ID NO.: 1, and (iii) cDNA according to (i) or (ii) above, and further comprising at least one attenuating mutation in said cDNA.

3. The recombinant DNA according to claim 1, wherein said cDNA has the sequence of SEQ ID NO.: 1.

4. The recombinant DNA according to claim 1, further comprising at least one attenuating mutation in said cDNA clone.

5. The recombinant DNA according to claim 1, further comprising at least two attenuating mutations in said cDNA clone.

6. The recombinant DNA according to claim 1, further comprising at least one attenuating mutation selected from the group consisting of codons at nsP1 amino acid position 538 which specify an attenuating amino acid, codons at E2 amino acid position 304 which specify an attenuating amino acid, codons at E2 amino acid position 314 which specify an attenuating amino acid, codons at E2 amino acid position 376 which specify an attenuating amino acid, codons at E2 amino acid position 378 which specify an attenuating amino acid, codons at nsP2 amino acid position 96 which specify an attenuating amino acid, and codons at nsP2 amino acid position 372 which specify an attenuating amino acid.

7. The recombinant DNA according to claim 1 further comprising at least one silent mutation.

8. The recombinant DNA according to claim 1, wherein not more than eight nucleotides are positioned between said promoter and said cDNA clone.

9. The recombinant DNA according to claim 1, wherein said recombinant DNA comprises a plasmid, and wherein said recombinant DNA further comprises a unique restriction site positioned downstream from said cDNA clone.

10. An infectious RNA transcript encoded by a cDNA according to claim 1.

11. The recombinant DNA according to claim 6, wherein said attenuating mutation comprises a substitution mutation.

12. The recombinant DNA according to claim 7, wherein said silent mutation is located at a position selected from the group consisting of nucleotide 215, nucleotide 3863, nucleotide 4196, nucleotide 4295, nucleotide 5972 and nucleotide 9113.

13. The recombinant DNA according to claim 8, wherein said promoter is selected from the group consisting of T3 promoters, T7 promoters, and SP6 promoters.

14. An infectious attenuated viral particle containing an infectious RNA transcript transcribed from a recombinant DNA, said recombinant DNA comprising a cDNA coding for an infectious South African Arbovirus No. 86 (S.A.AR86) virus RNA transcript, and a heterologous promoter positioned upstream from said cDNA and operatively associated therewith.

15. The infectious attenuated viral particles according to claim 14, wherein said cDNA is selected from the group consisting of (i) cDNA having the sequence of SEQ ID NO.: 1, (ii) cDNA encoding the same amino acid sequence encoded by the cDNA of SEQ ID NO.: 1, and (iii) cDNA according to (i) or (ii) above, and further comprising at least one attenuating mutation in said cDNA.

16. The infectious attenuated viral particles according to claim 14, wherein said cDNA has the sequence of SEQ ID NO.: 1.

17. The infectious attenuated viral particles according to claim 14, wherein said cDNA further comprises at least one attenuating mutation in said cDNA clone.

18. The infectious attenuated viral particles according to claim 14, wherein said cDNA further comprises at least two attenuating mutations in said cDNA clone.

19. The infectious attenuated viral particles according to claim 14, wherein said cDNA further comprises at least one attenuating mutation selected from the group consisting of codons at nsP1 amino acid position 538 which specify an attenuating amino acid, codons at E2 amino acid position 304 which specify an attenuating amino acid, codons at E2 amino acid position 314 which specify an attenuating amino acid, codons at E2 amino acid position 376 which specify an attenuating amino acid, codons at E2 amino acid position 378 which specify an attenuating amino acid, codons at nsP2 amino acid position 96 which specify an attenuating amino acid, and codons at nsP2 amino acid position 372 which specify an attenuating amino acid.

20. The infectious attenuated viral particles according to claim 14, wherein said recombinant DNA further comprises at least one silent mutation.

21. The infectious attenuated viral particles according to claim 14, wherein not more than eight nucleotides are positioned between said promoter and said cDNA.

22. The infectious attenuated viral particles according to claim 14, wherein said recombinant DNA comprises a plasmid, and wherein said recombinant DNA further comprises a unique restriction site positioned downstream from said cDNA.

23. The infectious attenuated viral particles according to claim 19, wherein said attenuating mutation comprises a substitution mutation.

24. The infectious attenuated viral particles according to claim 20, wherein said silent mutation is located at a position selected from the group consisting of nucleotide 215, nucleotide 3863, nucleotide 4196, nucleotide 4295, nucleotide 5972 and nucleotide 9113.

25. The infectious attenuated viral particles according to claim 24, wherein said promoter is selected from the group consisting of T3 promoters, T7 promoters, and SP6 promoters.

* * * * *

UNITED STATES PATENT AND TRADEMARK OFFICE
CERTIFICATE OF CORRECTION

PATENT NO. : 5,639,650
DATED : June 17, 1997
INVENTOR(S) : Johnston et al.

It is certified that error appears in the above-identified patent and that said Letters Patent is hereby corrected as shown below:

Col. 19, claim 15, line 8, replace "particles" with --particle--.

Col. 19, Claim 16, line 15, replace "particles" with --particle--.

Col. 19, Claim 17, line 18, replace "particles" with --particle--.

Col. 19, Claim 18, line 21, replace "particles" with --particle--.

Col. 19, Claim 19, line 23, replace "particles" with --particle--.

Col. 20, Claim 20, line 7, replace "particles" with --particle--.

Col. 20, Claim 21, line 11, eplace "particles" with --particle--.

Col. 20, Claim 22, line 15, eplace "particles" with --particle--.

Col. 20, Claim 23, line 20, replace "particles" with --particle--.

Col. 20, Claim 24, line 23, replace "particles" with --particle--.
Col. 25, claim 25, line 28, replace "particles" with --particle--.

Signed and Sealed this

Second Day of December, 1997

*Attest:*

BRUCE LEHMAN

*Attesting Officer*  *Commissioner of Patents and Trademarks*

UNITED STATES PATENT AND TRADEMARK OFFICE
CERTIFICATE OF CORRECTION

PATENT NO. : 5,639,650

DATED : June 17, 1997

INVENTOR(S) : Johnston et al.

It is certified that error appears in the above-identified patent and that said Letters Patent is hereby corrected as shown below:

Col. 1, after title, line 3', add -- This invention was made with government support under Federal Grant No. DAAL03-92-G-0084 from the U.S. Army Research Office. The government has certain rights in the invention.

Signed and Sealed this

Eleventh Day of May, 1999

Attest:

Attesting Officer

Q. TODD DICKINSON

Acting Commissioner of Patents and Trademarks